United States Patent [19]

Mark et al.

[11] 4,251,673
[45] Feb. 17, 1981

[54] RAPID HYDROLYSIS OF ESTERS

[75] Inventors: Harold W. Mark; William V. Childs, both of Bartlesville, Okla.

[73] Assignee: Phillips Petroleum Company, Bartlesville, Okla.

[21] Appl. No.: 54,532

[22] Filed: Jul. 3, 1979

[51] Int. Cl.³ .................. C07C 27/02; C07C 31/18; C07C 31/133; C07C 31/20
[52] U.S. Cl. .................. 568/858; 568/835; 568/853; 568/857; 568/877
[58] Field of Search ............ 568/858, 835, 853, 857, 568/877

[56] References Cited

U.S. PATENT DOCUMENTS

| | | | |
|---|---|---|---|
| 3,130,202 | 4/1964 | Robinson et al. | 568/858 |
| 3,647,892 | 3/1972 | Hoch | 568/858 |
| 3,652,656 | 3/1972 | Heywood et al. | 568/858 |
| 4,164,616 | 8/1979 | Childs | 568/858 |

Primary Examiner—Joseph E. Evans

[57] ABSTRACT

An organic ester e.g. 1,4-diacetoxybutane is hydrolyzed with an alkali metal or an alkaline earth metal hydroxide to a corresponding alcohol, the reaction being rapidly effected by having present a hydroxyl-containing compound. In a preferred embodiment, the hydroxyl-containing compound to be present is the very compound to be produced e.g. 1,4-butanediol is to be produced from 1,4-diacetoxybutane and there is present during the reaction of hydrolysis an earlier produced 1,4-butanediol.

11 Claims, 1 Drawing Figure

TEMPERATURE REACHED DURING HYDROLYSIS OF 1,4-DIACETOXYBUTANE

EXAMPLE II. 10.57 g 1,4-DIACETOXYBUTANE
          + 15.3 g 50 WT. % AQ. KOH
EXAMPLE III. 10.57 g 1,4-DIACETOXYBUTANE
           + 15.3 g 50 WT. % AQ. KOH
           + 10.0 g 1,4-BUTANEDIOL

TEMPERATURE REACHED DURING HYDROLYSIS OF 1,4-DIACETOXYBUTANE

EXAMPLE II. 10.57 g 1,4-DIACETOXYBUTANE
+ 15.3 g 50 WT. % AQ. KOH
EXAMPLE III. 10.57 g 1,4-DIACETOXYBUTANE
+ 15.3 g 50 WT. % AQ. KOH
+ 10.0 g 1,4-BUTANEDIOL

RAPID HYDROLYSIS OF ESTERS

BRIEF SUMMARY OF THE INVENTION

Hydrolysis of an organic ester with an alkali and/or an alkaline earth metal hydroxide to form the corresponding alcohol is rapidly effected in presence of a hydroxyl-containing compound.

BRIEF DESCRIPTION OF THE DRAWINGS

The drawing shows the temperature reached during hydrolysis of 1,4-diacetoxybutane in the presence of 1,4-butanediol. The temperature reached during hydrolysis is plotted against time.

DETAILED DESCRIPTION

Figure 1:
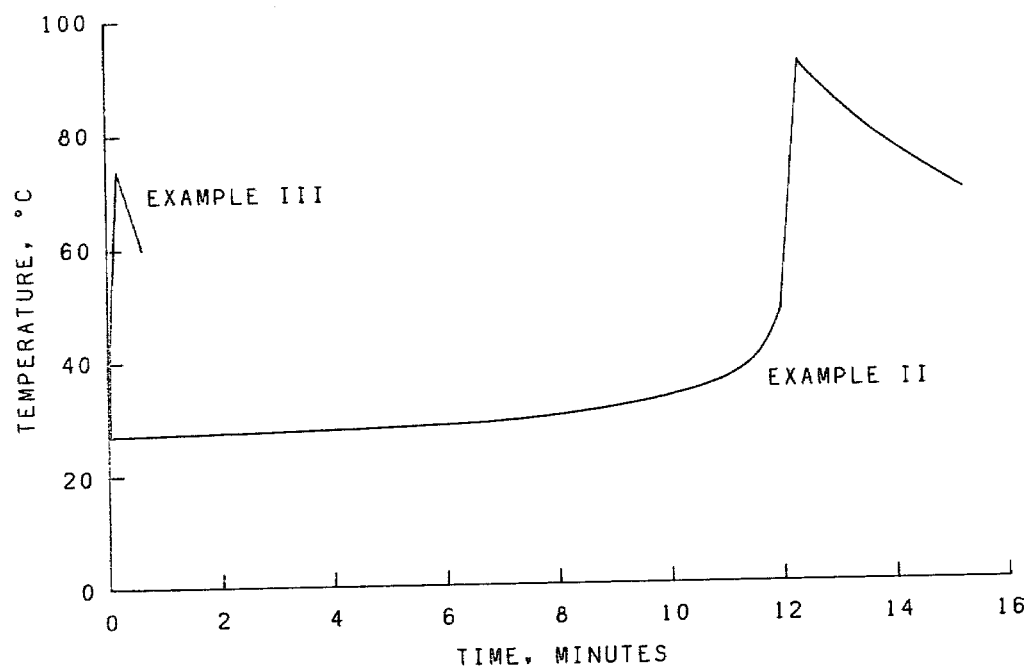

This invention relates to the hydrolysis of an organic ester. In one of its aspects the invention relates to the hydrolysis of an organic ester with an alkali and/or an alkaline earth metal hydroxide to form a corresponding alcohol.

In one of its concepts, the invention provides a process for the rapid hydrolysis of an organic ester with an alkali an/or an alkaline earth metal hydroxide to a corresponding alcohol by having present, initially, for the hydrolysis reaction a hydroxyl-containing compound. In another of its concepts, the invention provides a process as described herein wherein the hydroxyl-containing compound which is to be present during the hydrolysis reaction is the very compound which is to be formed during the hydrolysis. In a more specific concept of the invention, in one embodiment thereof, 1,4-diactoxybutane is hydrolyzed in the presence of 1,4-butanediol, to form the latter compound.

Butanediols, particularly 1,4-butanediols, are becoming increasingly important in recent years because they form polyesters with terephthalic acid which are useful molding materials having excellent physical properties. Butanediols are also used as starting materials for commercially valuable chemicals such as tetrahydrofuran, γ-butyrolactone and the like.

It is known that butanediol or butenediol can be prepared by hydrolyzing the corresponding diacetoxy derivative. U.S. Pat. No. 3,917,720, issued Nov. 4, 1975, discloses hydrolyzing a diol diester with water, using an acid cation-exchange resin as the catalyst. Part of the acid segments of the resin is eluted in the resulting liquid which may unfavorably affect the thermostability of the diol.

U.S. Pat. No. 3,968,174, issued July 6, 1976, discloses a disproportionation reaction between a carboxylate monoester, an alkanoic acid, and an alkali metal acetate which produces a diol and a lower melecular weight ester which is difficult to separate and generally is a useless by-product that must be disposed of in some unprofitable manner.

U.S. Pat. No. 4,062,900, issued Dec. 13, 1977, discloses an acid catalyzed hydrolysis driven by the removal of a product by distillation. The reaction requires external heating and an extra ion exchange resin treatment step.

U.S. Pat. NO. 4,036,895, issued July 19, 1977, describes the base catalyzed hydrolysis of a diol diacetate to the corresponding diol by adding alkanols ranging from 1–4 carbon atoms. The process requires large amounts of alkanols present which requires additional and timeconsuming separations.

Although the above processes produce, for the most part, high yields of the desired diols, they all possess a common disadvantage in that a significant amount of time and a separate reactor as well as a separate reaction step is required to conduct the hydrolysis. A significant economic advantage desirable to attain is to reduce the time for the hydrolysis thus to make it an immediate or nearly instantaneous reaction. This would eliminate the need for a separate hydrolysis step or reactor to conduct the hydrolysis. Thus, the hydrolysis would occur within, for example, transfer lines from an acetoxylation reactor to a diol separator or fractionator.

It is an object of this invention to provide a process for hydrolysis of an organic ester. It is another object of this invention to improve the rate of reaction of an organic ester hydrolysis step. It is a further object of the invention to provide a process for hydrolyzing an organic ester with an alkali and/or an alkaline earth metal hydroxide to form a corresponding alcohol. It is a still further object of the invention to provide a simplified handling of reactants during a hydrolysis as herein described. Further, it is an object of the invention to substantially completely eliminate a separate hydrolysis and/or separate reactor in which to conduct hydrolysis.

Other aspects, concepts, and objects are apparent from a study of this disclosure, the drawing and the appended claims.

According to the present invention, there is provided a process for the hydrolysis of an organic ester with an alkali and/or an alkaline earth metal hydroxide to form a corresponding alcohol there being present during the hydrolysis reaction, preferably initially present, a hydroxyl-containing compound.

Also according to the invention, it is now preferred to have present at the outset of the reaction a portion of the very alcohol to be produced by that reaction. Thus, in one of its embodiments, the invention provides a method for the preparation of organic hydroxy-containing materials by the alkali and/or an alkaline earth metal hydroxide hydrolysis of the corresponding ester in a reaction medium containing a hydroxyl-containing compound, herein described.

As can be seen from the graph in the figure of the drawing, the invention provides a very considerable increase in the rate of the ester hydrolysis.

ESTER FEEDSTOCK

Esters useful in this invention for hydrolysis to the corresponding alcohols are those represented by the following general formula $$R-(OR')_n$$

wherein R can be any hydrocarbyl radical having a valence equal to n and can contain 1 to 10 carbon atoms; R' can be any alkanoyl or cycloalkanoyl radical and can contain 1 to 10 carbon atoms, preferably 1 to 4 carbon atoms; and n can be an integer of 1 to 4.

Typical compounds representing these type materials are, for example.

| where n = 1 | |
|---|---|
| methyl formate | 1,2-diacetoxybutane |
| ethyl acetate | 1,2-diacetoxy-3-butene |
| propyl propionate | 1,3-diacetoxybutane |

| | | | |
|---|---|---|---|
| | butyl acetate | | 1,4-diacetoxybutane |
| | butenyl acetate | | 1,4-diacetoxy-2-butene |
| | butyl butyrate | | 1,5-diacetoxypentane |
| | hexyl acetate | | 1,5-dipropanoyloxy-3-pentene |
| | hexyl hexanoate | | 1,5-dibutanoyloxy-3-pentene |
| | cyclohexyl acetate | | 1,10-diacetoxydecane |
| | decyl decanoate | where n = 3 | 1,2,4-triacetoxybutane |
| where n = 2 | 1,2-diacetoxyethane | | 1,2,6-triacetoxyhexane |
| | 1,2-diacetoxypropane | | 2-ethyl-2-acetoxymethyl-1, 3-diacetoxypropane |
| | 1,3-diacetoxypropane | | 2-acetoxymethyl-2-methyl-1, 3-diacetoxypropane |
| | 1,2-diacetoxy-2-propene | | |
| | | where n = 4 | 2,2-bis(acetoxymethyl)-1, 3-diacetoxypropane |
| | | | 1,2,3,4-tetraacetoxybutane | and the like, and mixtures thereof.

HYDROXYL-CONTAINING COMPOUNDS AS RATE INCREASING AGENTS

Hydroxyl-containing compounds useful in this invention as hydrolysis rate enhancing agents include those materials represented by the following formulas

| R″—OH | HO—(R‴—O)$_m$—H | HO—R″″—OH |
|---|---|---| wherein R″ can be an alkyl or alkenyl radical containing 1 to 4 carbon atoms; R‴ can be any alkylene or alkenylene radical containing 1 to 4 carbon atoms; R″″ can be any alkylene or alkenylene radical containing 2 to 8 carbon atoms; and m can be 1 to about 80.

The mono- and dihydroxy compounds herein described that are used as rate enhancing agents must be at least about 10 wt. % soluble in water so that during the hydrolysis step intimate contact can be made between the hydroxy compound and the inorganic base.

Typical compounds representing these type materials are, for example,

| | |
|---|---|
| methyl alcohol | ethylene glycol |
| ethyl alcohol | triethylene glycol |
| n-propyl alcohol | tetraethylene glycol |
| isopropyl alcohol | pentaethylene glycol |
| n-butyl alcohol | polyethylene glycol, 200* |
| sec-butyl alcohol | polyethylene glycol, 300 |
| tert-butyl alcohol | polyethylene glycol, 400 |
| 1,2-ethanediol | polyethylene glycol, 600 |
| 1,2-propanediol | polyethylene glycol, 1000 |
| 1,3-propanediol | polyethylene glycol, 1500 |
| 1,2-butanediol | polyethylene glycol, 4000 |
| 1,3-butanediol | polyethylene glycol, 6000 |
| 2-butene-1,4-diol | polypropylene glycol, 150 |
| 1,4-butanediol | polypropylene glycol, 400 |
| 1,5-pentanediol | polypropylene glycol, 425 |
| 1,6-hexanediol | polypropylene glycol, 750 |
| 1,7-heptanediol | |
| 1,8-octanediol | |

*Numbers indicate mol. wts.

and the like, and mixtures thereof.

The amount of hydroxy compound present can be broadly 1–100 wt. % based on the amount of ester, R(OR′)$_n$, present but 5–50 wt. % is now preferred. It is now preferred that the hydroxy-containing rate enhancement agent be the same as the hydroxy product obtained from the hydrolysis of the ester to facilitate subsequent separations and purifications.

A concept basic to this invention is the finding that the use of a hydroxy compound, as described, will increase the rate of the hydrolysis reaction. Mere routine testing will determine whether any particular hydroxy compound will sufficiently or desirably enhance the rate of the hydrolysis reaction.

INORGANIC BASES

The inorganic bases useful in this invention are limited to the alkali and alkaline earth metal hydroxides and ammonium hydroxide. Presently, herein and in the claims alkali and/or an alkaline earth metal hydroxide is inclusive of ammonium hydroxide, the alkali metal hydroxides and ammonium hydroxide are preferred because of their greater solubility in water. Also, those metal hydroxides having the greater water solubilities can be employed at higher concentrations, thus providing greater hydrolyzed ester productivity because of the smaller water volume required.

Inorganic bases most useful in this invention are LiOH, NaOH, KOH, RbOH, CsOH, and NH$_4$OH. The selection of the optimum inorganic hydroxide is left to the user. However, when the basic hydrolysis described herein is part of a multi-step process to make 1,4-butanediol as disclosed in pending application, Ser. No. 870,157, filed Jan. 17, 1978, now allowed, it is preferred to employ the same metal cation as used in earlier steps of the above mentioned application.

This metal cation is in a recycling process in which, for example, potassium acetate is converted to potassium bromide which in turn is converted to potassium hydroxide which is then converted to potassium acetate, the later conversion being in the present invention.

The amount of inorganic base required in the current invention should be at least stoichiometric to the amount of ester groups available for hydrolysis for complete conversion. Thus, the mole ratio of inorganic base to hydrolyzable ester groups can be 1:1 to 1.5:1 although only a slight excess of base is necessary. Thus, the preferred mole ratio range is 1.01:1 to 1.2:1.

REACTION CONDITIONS

The reaction temperature of the invention is not critical and can be run initially near or slightly below ambient room temperature to about 120° C. Since the reaction is already exothermic, there does not appear to be any advantage in conducting the reaction above 120° C. Likewise, the reaction can be effected under vacuum, atmospheric, or under whatever pressure is convenient. The increased reaction rates described herein permit the ester hydrolysis to be conducted either in a batchwise or continuous fashion. When continuous, the ester hydrolysis can be carried out in a tubular reactor or even in a transfer line leading from one vessel to another. When the latter is employed some type of static or other mixer will assure enough turbulence if mixing is otherwise inadequate.

EXAMPLE I - PREPARATION OF 1,4-DIACETOXYBUTANE

This example describes the preparation of 1,4-diacetoxybutane used to demonstrate the operability of this invention. Into a 2-liter round bottom flask fitted with a magnetic stirrer, reflux condenser, thermometer and dropping funnel was charged 1100 grams (10.77 moles) acetic anhydride and heated to reflux (139° C.) whereupon 450 grams (4.99 moles) of 1,4-butanediol was rapidly added with vigorous stirring. The mixture was stirred for 1 hour above 100° C. The contents were cooled to room temperature and excess acetic anhydride and acetic acid by-product removed under vacuum (15-20 millimeters) while a stream of nitrogen was passed through the system (head temperature varied from 28° C. to about 100° C. The product, 1,4-diacetoxybutane, was then removed by flash distillation using a rotovapor apparatus at about 80°-85° C./1 mm vacuum. The overhead product was analyzed by comparison of retention time with an authentic sample of 1,4-diacetoxybutane using a 6 ft. glass Gas Liquid Chromatography (GLC) column, packed with 20 M Carbowax on Teflon and programmed between 100° C. to 220° C./min., helium flow 30 cc/min.

EXAMPLE II - HYDROLYSIS WITHOUT HYDROLYZED PRODUCT

This example is a control run and illustrates the rate of hydrolysis of 1,4-diacetoxybutane in the absence of the corresponding hydrolyzed product. Into a 100 milliliter graduate was added 15.3 grams (0.136 moles) of a 50 wt. % aqueous KOH solution and 10 milliliters (10.57 grams, 0.0607 moles) of 1,4-diacetoxybutane. A stirrer was positioned at the interface between the two liquid phases with a thermometer slightly above the stirrer. While the solution was vigorously stirred, the time and temperature was recorded. The data which is listed in Table I below shows a slow increase in temperature such that in about 12.5 minutes a maximum temperature was reached. The time to reach this temperature was considered to be the time required to completely hydrolyze the 1,4-diacetoxybutane. Analysis by GLC confirmed the formation of 1,4-butanediol and the complete hydrolysis of 1,4-diacetoxybutane.

TABLE I

| Time, mins. | 1 | 6 | 10 | 11 | 12 | 12.4 | 12.7 | 13 | 14 | 15 |
|---|---|---|---|---|---|---|---|---|---|---|
| Temp. °C. | 27 | 29 | 33 | 35 | 46 | 91 | 86 | 83 | 76 | 70 |

EXAMPLE III - HYDROLYSIS IN PRESENCE OF HYDROLYZED PRODUCT

This example illustrates the invention and demonstrates the increase in the rate of hydrolysis of 1,4-diacetoxybutane in the presence of the corresponding hydrolyzed product. The procedure described in Example II was repeated except the charge was 15.3 grams (0.136 moles) of a 50 wt. % aqueous KOH solution, 10 milliliters (10.57 grams, 0.0607 moles) of 1,4-diacetoxybutane, and 10 grams of 1,4-butanediol. After mixing an almost immediate exotherm resulted making it nearly impossible to accurately record a time-temperature profile. Nevertheless, an approximate maximum temperature of about 75° C. was reached in 20 seconds. Again, GLC analysis confirmed the complete conversion of 1,4-diacetoxybutane to 1,4-butanediol.

The example was repeated on a larger scale using proportionately less 1,4-butanediol in the initial charge. To a 250 milliliter graduate was added 153 g (1.36 moles) of a 50 wt. % aqueous KOH solution, 100 milliliters (105.7 grams, 0.607 moles) of 1,4-diacetoxybutane and 50.0 grams of 1,4-butanediol. Again, the hydrolysis as measured by a maximum temperature increase was complete within 60 seconds. The product was subjected to vacuum distillation, 127° C./20 mm. The identity of this overhead was confirmed on GLC as 1,4-butanediol by comparison with an authentic sample.

EXAMPLE IV - HYDROLYSIS WITH OTHER HYDROXY-CONTAINING COMPOUNDS

This example illustrates the use of other hydroxy-containing compounds to enhance the hydrolysis rate of 1,4-diacetoxybutane. The procedure described in Example III was repeated 3 times except that each time a different hydroxy-containing compound was present during the hydrolysis. In each case the hydrolysis of 1,4-diacetoxybutane to 1,4-butanediol, as measured by increase in temperature, was almost immediate and complete in less than 60 seconds. Table II below lists the different hydroxy-containing compounds employed along with the amounts of ingredients.

TABLE II

| Run No. | 1 | 2 | 3 |
|---|---|---|---|
| 1,4-Diacetoxybutane | 10.57 g | 10.57 g | 10.57 g |
| 50 wt. % Aqueous KOH | 15.3 g | 15.3 g | 15.3 g |
| Hydroxy-Containing Additive | 10.0 g | 10.0 g | 10.0 g |
|  | Methyl Alcohol | Ethyl Alcohol | Ethylene Glycol |
| Time to reach maximum exotherm, mins. | Immediate | Immediate | Immediate |

The invention is graphically summarized in FIG. 1 wherein it is shown that the hydrolysis of organic esters such as 1,4-diacetoxybutane can be accomplished in a very short time, almost immediately, when a hydroxy-containing compound is present in the hydrolysis mixture. Because of this very short reaction time, the current invention lends itself very well to a continuous process. Also, the increased reaction rate may permit the reaction to be effected in a transfer line transferring the reactants one vessel to another, thus eliminating a separate step effected in a separate reactor.

Reasonable variation and modification are possible within the scope of the foregoing disclosure, drawing and the appended claims to the invention the essence of which is that an organic ester is hydrolyzed with at least one of an alkali and alkaline earth metal hydroxide there being present during the hydrolysis reaction, preferably ab initio, a hydroxyl-containing compound, said compound preferably being the compound being produced.

We claim:

1. A process for causing the almost immediate inorganic base-catalyzed conversion at about room temperature of an organic carboxylic ester by hydrolysis of said ester to the corresponding organic hydroxyl-containing compound by adding to the reaction mass a hydrolysis reaction rate increaser and reacting said ester in said mass containing said reaction rate increaser with an inorganic base which is at least one of an alkali and alkaline earth metal hydroxide thus initiating an exothermic reaction, said hydrolysis rate increaser being present in an amount broadly 5-50 weight percent of said ester and being an organic hydroxyl-containing compound selected from materials represented by the following formulas

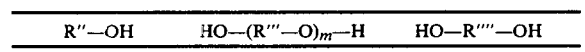

wherein R" can be an alkyl or alkenyl radical containing 1 to 4 carbon atoms; R'" can be any alkylene or alkenylene radical containing 1 to 4 carbon atoms; R"" can be any alkylene or alkenylene radical containing 2 to 8 carbon atoms; and m can be 1 to about 80.

2. A process according to claim 1 wherein the hydroxyl-containing compound is the organic hydroxyl containing-compound to which the organic ester is to be hydrolyzed.

3. A process according to claim 1 wherein the compound to be produced is 1,4-butanediol.

4. A process according to claim 2 wherein the compound to be produced is 1,4-butanediol.

5. A process according to claim 1 wherein the ester to be hydrolyzed is at least one of those represented by the following general formula $$R\text{-}(OR')_n$$

wherein R can be any hydrocarbyl radical having a valence equal to n and can contain 1 to 10 carbon atoms; R' can be any alkanoyl or cycloalkanoyl radical and can contain 1 to 10 carbon atoms, preferably 1 to 4 carbon atoms; and n can be an integer of 1 to 4.

6. A process according to claim 1 wherein the organic ester is 1,4-diacetoxybutane and the inorganic base is an alkali and/or alkaline earth metal hydroxide.

7. A process according to claim 1 wherein the inorganic base is ammonium hydroxide.

8. A process according to claim 6 wherein the hydroxy-containing compound is 1,4-butanediol.

9. A process according to claim 7 wherein the hydroxy-containing compound is 1,4-butanediol.

10. A process according to claim 1 wherein the organic hydroxyl compound is the organic hydroxyl-containing compound to which the organic ester is to be hydrolyzed.

11. A process according to claim 10 wherein the organic hydroxyl-containing compound is 1,4-butanediol.

* * * * *